US012662399B2

(12) United States Patent
Pawlow et al.

(10) Patent No.: US 12,662,399 B2
(45) Date of Patent: Jun. 23, 2026

(54) DRINKING WATER DISPENSER WITH BUILT-IN UV STERILIZATION SYSTEM

(71) Applicant: Scandinavian Innovation Group Oy, Pomarkku (FI)

(72) Inventors: Andrzej Pawlow, Riga (LV); Arturs Pavlovs, Riga (LV)

(73) Assignee: Scandinavian Innovation Group Oy, Pomarkku (FI)

( * ) Notice: Subject to any disclaimer, the term of this patent is extended or adjusted under 35 U.S.C. 154(b) by 96 days.

(21) Appl. No.: 18/862,201

(22) PCT Filed: Apr. 30, 2023

(86) PCT No.: PCT/IB2023/054501
§ 371 (c)(1),
(2) Date: Nov. 1, 2024

(87) PCT Pub. No.: WO2023/214283
PCT Pub. Date: Nov. 9, 2023

(65) Prior Publication Data
US 2025/0340461 A1      Nov. 6, 2025

(30) Foreign Application Priority Data
May 3, 2022     (EP) ..................................... 22171251

(51) Int. Cl.
*C02F 1/32*          (2023.01)
*A61L 2/10*         (2006.01)
*B67D 3/00*        (2006.01)

(52) U.S. Cl.
CPC ................ *C02F 1/325* (2013.01); *A61L 2/10* (2013.01); *B67D 3/0009* (2013.01);
(Continued)

(58) Field of Classification Search
CPC ................ C02F 1/325; C02F 2201/005; C02F 2201/3221; C02F 2201/3228;
(Continued)

(56) References Cited

U.S. PATENT DOCUMENTS

| | | | |
|---|---|---|---|
| 5,441,179 A | 8/1995 | Marsh | |
| 6,139,726 A * | 10/2000 | Greene | ..................... C02F 9/20 210/97 |

(Continued)

FOREIGN PATENT DOCUMENTS

| | | | | |
|---|---|---|---|---|
| CA | 2435587 A1 * | 1/2005 | | |
| CN | 1867802 A * | 11/2006 | ................ | C02F 9/20 |
| CN | 110382401 A * | 10/2019 | .............. | B67D 1/07 |
| EP | 1270501 A1 * | 1/2003 | .......... | B67D 1/0009 |
| JP | 2010076815 A | 4/2010 | | |
| WO | 2017221719 A1 | 12/2017 | | |

*Primary Examiner* — Bob Zadeh
(74) *Attorney, Agent, or Firm* — Smartpat PLC

(57) ABSTRACT

A water dispenser with built-in UV sterilization system includes a tap, and a water tank with a cooling device. An inlet connects the tank to a water source. A UV radiation source is installed inside the cold water tank. A cooled water outlet is connected to the tap. The dispenser contains a flow sterilizer with an inlet connected to an outlet of the tank for uncooled water. An outlet of the sterilizer is connected to a sterilized water inlet of the tank. A funnel is installed inside the cold water tank under a water source inlet. An upper edge of the funnel is above a water level in the tank, to isolate water in a lower part of the tank from unsterilized water coming from the source. A narrow lower part of the funnel is connected to the outlet for uncooled water.

12 Claims, 5 Drawing Sheets

(52) U.S. Cl.
CPC ...... *A61L 2202/11* (2013.01); *A61L 2202/121* (2013.01); *A61L 2202/122* (2013.01); *A61L 2202/123* (2013.01); *C02F 2201/005* (2013.01); *C02F 2201/3221* (2013.01); *C02F 2201/3228* (2013.01); *C02F 2209/42* (2013.01); *C02F 2303/04* (2013.01); *C02F 2307/10* (2013.01)

(58) Field of Classification Search
CPC .............. C02F 2209/42; C02F 2303/04; C02F 2307/10; A61L 2/10; A61L 2202/11; A61L 2202/121; A61L 2202/122; A61L 2202/123; B67D 3/0009; B67D 3/0077; B67D 2210/00007; B67D 2210/00013; B67D 2210/00015; B67D 3/0035; B67D 3/0038; B67D 3/0074; B67D 3/0029
See application file for complete search history.

(56) References Cited

U.S. PATENT DOCUMENTS

| | | | |
|---|---|---|---|
| 6,483,119 B1 | 11/2002 | Baus | |
| 8,334,518 B2* | 12/2012 | Matsuda | B67D 1/0857 |
| | | | 250/435 |
| 2004/0074252 A1* | 4/2004 | Shelton | C02F 9/20 |
| | | | 222/190 |
| 2010/0005825 A1* | 1/2010 | Yui | B67D 3/0032 |
| | | | 422/305 |
| 2010/0200769 A1 | 8/2010 | Matsuda et al. | |
| 2015/0360978 A1* | 12/2015 | Davis | C02F 1/50 |
| | | | 210/764 |
| 2016/0083242 A1* | 3/2016 | Groesbeck | B67D 3/0032 |
| | | | 222/173 |
| 2016/0278424 A1* | 9/2016 | Liao | B67D 3/0032 |
| 2024/0239691 A1* | 7/2024 | Pawlow | B67D 3/0058 |
| 2025/0340461 A1* | 11/2025 | Pawlow | B67D 3/0035 |

* cited by examiner

DRINKING WATER DISPENSER WITH BUILT-IN UV STERILIZATION SYSTEM

CROSS-REFERENCE TO RELATED APPLICATION

This application is a national stage application, filed under 35 U.S.C. § 371, of International Patent Application PCT/IB2023/054501, filed on Apr. 30, 2023, which claims the benefit of European Patent Application EP 22171251.6, filed on May 3, 2022.

TECHNICAL FIELD

The disclosure relates to drinking water dispensers, in particular to dispensers equipped with UV water sterilization devices.

BACKGROUND

Drinking water dispenser or cooler is a device for dispensing cooled drinking water to consumers. Water from the external source, for example, a bottle or water-pipe, enters the cold water tank, where it is cooled to a set temperature, usually 4-10 degrees, and is dispensed from the cold water tank to consumers through a tap or valve.

Water entering the dispenser from the source may contain pathogens, the presence of which in water dispensed to consumers is undesirable. Air entering the dispenser from the room may be another source of pathogens. Even a small number of pathogens entering water can lead to the development of unfavorable microbiological environment in the cold water tank.

It is known to use UV radiation, for example from UV LEDs located in the cold tank, to sterilize water in the cold tank or to suppress the development of microbiological environment in the cold tank. Such dispensers are described, for example, in US2016/0278424 A1, U.S. Pat. No. 6,483,119 B1 or WO2017/221719.

However, water sterilization in the cold water tank using UV LED radiation is only possible with low concentrations of pathogens. If a large number of pathogens enter the cold tank or if the UV radiation is turned off for a long time, the number of pathogens may rise to the extent that the UV LED radiation power is not sufficient to sterilize the entire volume of water in the tank.

In the documents U.S. Pat. Nos. 5,441,179 and 6,139,726 is proposed using a lamp as the source of UV radiation. However, placing the lamp in the cold tank significantly complicates the design of the cold tank, since it is necessary not only to protect the lamp from possible damage, but also to exclude the possibility of substances harmful to humans entering the water if the lamp is damaged.

Besides, with high radiation power the lamp gives the water a "burnt" taste.

Another common disadvantage of devices with the UV radiation source in the cold water tank, whether it is a lamp or LEDs, is that when water is dispensed from the cold water tank, the tank is simultaneously filled up from the source. As unsterilized water coming from the source is actively mixed with water in the tank a part of unsterilized water from the source can be dispensed to consumers.

Moreover, such method of sterilizing water in the cold water tank is inefficient, since a large amount of water must be constantly treated. If even a small amount of unsterilized water is added to the cold water tank, all water in the tank must be treated.

Thus, there is a need to improve the efficiency of sterilization of water in the dispenser, especially in the cold water tank, and to reduce or eliminate the shortcomings of known devices.

SUMMARY

The mentioned problems, at least in part, are solved in a drinking water dispenser with UV sterilization system comprising a housing and the installed in the housing: a device for connecting to a water source; a tap for dispensing cooled water to consumers; a cold water tank equipped with a cooling device and having a lower part filled with water and an upper part where an air cavity is formed when the tank is filled with water, the cold water tank has an inlet for water coming from the source connected to the device for connecting to the water source; at least one UV radiation source is installed inside the cold water tank; the cold water tank has a cooled water outlet connected to the tap for dispensing cooled water to consumers. The dispenser additionally comprises a flow sterilizer having an inlet and outlet; the cold water tank is additionally equipped with an outlet for uncooled water and an inlet for sterilized water; the inlet of the flow sterilizer is connected to the outlet for uncooled water, and the outlet of the flow sterilizer is connected to the inlet for sterilized water. A funnel having a wide upper part and a narrow lower part is installed inside the cold water tank. The funnel is installed under the inlet for water coming from the source, so that an upper edge of the funnel is above the water level in the tank, to isolate water in the lower part of the tank from unsterilized water coming from the source, and the narrow lower part of the funnel is connected to the outlet for uncooled water.

The dispenser is preferably adapted for use of upturned bottle on top of the device as the source of water, and the device for connecting to the water source contains a bottle receiver for installation of the upturned bottle and a water intake finger, a water channel of which forms the inlet for water coming from the source.

The dispenser can also be used with other water sources, for example, the device for connection to the water source may contain means for connection to a bag-in-box water source or means for connection to a water-pipe.

In this case, it is convenient to equip the dispenser with a water level sensor installed in the cold water tank and connected to an electronic control device to maintain the pre-set water level.

The dispenser preferably contains a tap for dispensing uncooled water to consumers connected to the outlet of the flow sterilizer and a check valve installed between the flow sterilizer and the inlet for sterilized water to prevent water coming from the cold water tank in the uncooled water dispensing mode. In this configuration, the common flow sterilizer is used both to sterilize the water coming into the cold water tank and the uncooled water dispensed to consumers.

It is preferable to place the UV radiation sources located in the cold water tank in the upper part of the cold water tank. Placement of the UV radiation sources above the water level, in the air cavity of the cold water tank, first, simplifies the design of the UV radiation sources, and, second, allows to also treat the air supplied to the bottle using UV radiation, which protects the water in the bottle from pathogens coming from the atmosphere.

It is preferable to place at least one UV radiation source in the cold water tank in such a way that part of its radiation enters the funnel, thereby also preventing the development of pathogens inside the funnel.

It is convenient to position the flow sterilizer in such a way that part of UV radiation from the flow sterilizer enters the lower part of the funnel. At the same time, it is desirable to make the lower part of the funnel in form of a vertical pipe and make its inner walls from a material reflecting UV radiation. With this positioning, the sterilization of water will be at least partially carried out in the funnel.

It is preferable to place the flow sterilizer at least partially in the cold water tank. Placement of the flow sterilizer partially in the cold water tank, i.e., in the lower part of the funnel located in the cold water tank, allows to reduce the overall height of the dispenser.

DETAILED DESCRIPTION

Figure 1:
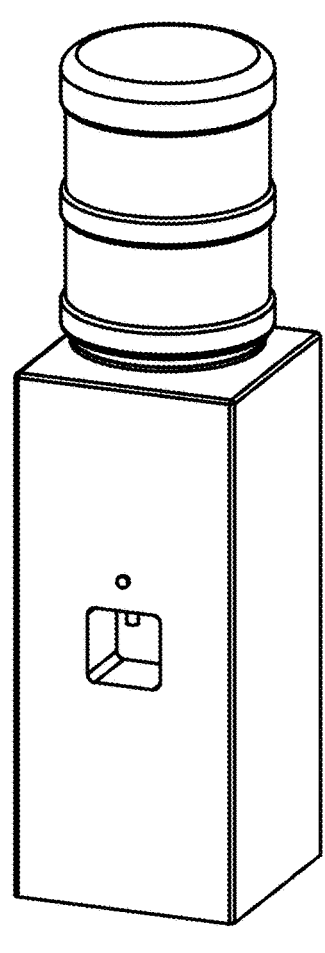
FIG. 1 shows a general view of the dispenser with upturned bottle.
Figure 3:
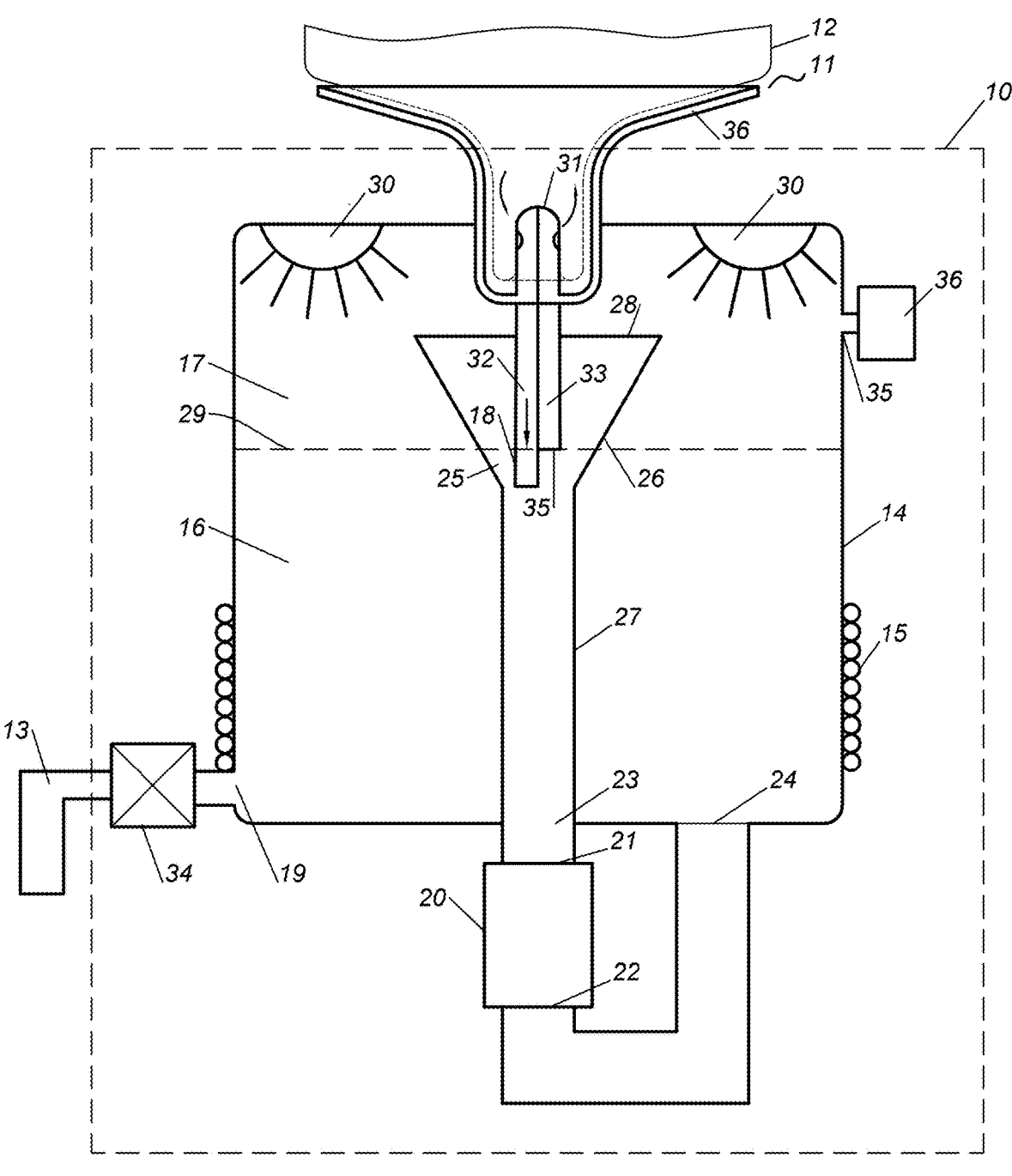
FIG. 3 schematically shows the interior design of the proposed dispenser.

The first embodiment offers drinking water dispenser with the bottle as a water source. A general view of such dispenser is shown in FIG. 1 and its interior design is schematically shown in FIG. 3. This dispenser uses the upturned bottle 12 as the source of water. The dispenser consists of the housing 10, in the upper part of which the bottle receiver 11 is installed, in which the bottle with drinking water 12 turned down with its neck is installed. The water intake finger 31 is installed in the lower part of the bottle receiver 11, through which water from the bottle 12 enters the cold water tank 14.

The cold water tank 14 is equipped with the cooling device 15. To dispense the cold water to consumers, the cold water tank 14 has the outlet 19, which is connected to the tap 13 through the solenoid valve 34.

The cold water tank 14 has the lower part 16 filled with water and the upper part 17, where air cavity is formed. The upper part 17 is connected to the atmosphere through the air inlet 35 and the air filter 36.

The water intake finger 31 has two separate channels, the water channel 32, through which water from the bottle enters the cold water tank 14, and the air channel 33, through which air enters the bottle 12 from the upper part 17 of the water tank 14.

Water from the water channel 32 of the water intake finger 31 enters the tank 14 through the inlet 18. Under the inlet 18 for the water entering the tank 14, the funnel 25 is installed. The funnel 25 is turned with its wide part 26 up and installed in such a way that unsterilized water coming from the bottle 12 enters the funnel 25 and does not come to the sterilized water in the tank 14. The lower narrow part 27 of the funnel 25 is connected to the uncooled water outlet 23, which is connected to the inlet 21 of the flow sterilizer 20. The outlet 22 of the flow sterilizer 20 is connected to the inlet 24 for sterilized water.

Any flow sterilizer of suitable capacity can be used as a flow sterilizer. It is preferable to use a flow sterilizer, where sterilization of flowing water is carried out using semiconductor ultraviolet radiation sources.

The funnel 25 is installed in the cold water tank 14 so that its upper edge 28 is always above the water level 29. The outlet 18 of the water channel 32 and the inlet 35 of the air channel of the water intake finger 31 are inside the upper wide part 26 of the funnel 25. Thus, all water from the bottle 12 passes through the funnel 25, which prevents the unsterilized water coming from the bottle into the sterilized water in the tank 14.

One or several UV radiation sources 30 are located in the cold water tank 14 in its upper part 17. UV radiation sources 30 are located above the water level 29 and above the upper edge 28 of the funnel 25, so that part of the UV radiation comes into the funnel 25 thereby preventing the development of pathogens inside the funnel 25. The UV sources 30 are located on different sides of the funnel 25 so that the funnel does not obscure the interior of the tank 14 and all water in the tank 14 is illuminated by the radiation of UV sources 30.

During the operation of the dispenser, the unsterilized water from the bottle entering the dispenser through the water intake finger 31 comes into the funnel 25, from where it comes to the flow sterilizer 20 through the outlet 23, and the sterilized water that has passed through the flow sterilizer 20 enters the cold water tank 14 through the inlet 24. The sterilized water is cooled to a set temperature, usually 4-10° C., in the cold water tank 14.

Cooled water is dispensed to consumers through the outlet 19, valve 34 and tap 13. When water is dispensed to consumers from the tap 13, the same amount of water enters the water tank 14 from the bottle 12. Maintaining the water level 29 in the tank 14 is controlled through the air channel 33 of the water intake finger 31. Since the funnel 25 and the tank 14 form communicating vessels, the water in the funnel 25 is at the same level 29 as in the tank 14. As soon as the water level 29 in the tank 14 and, accordingly, in the funnel 25 falls below the inlet 35 of the air channel 33, the water from the bottle 12 starts flowing into the funnel 25, and enters the lower part 16 of the cold water tank through the flow sterilizer 20, the water level in the tank 14 rises, respectively, the water level in the funnel 25 rises, and when the water covers the inlet 35 of the air channel 33 of the water intake finger 31, the flow of water from the bottle 12 stops.

Thus, during the operation of the dispenser, all water entering the cold water tank 14 from the bottle 12 is sterilized by flowing through the flow sterilizer 20. The sterilized water in the tank 14 is maintained sterile using UV radiation from the sources 30 located in the tank 14.

Figure 4:
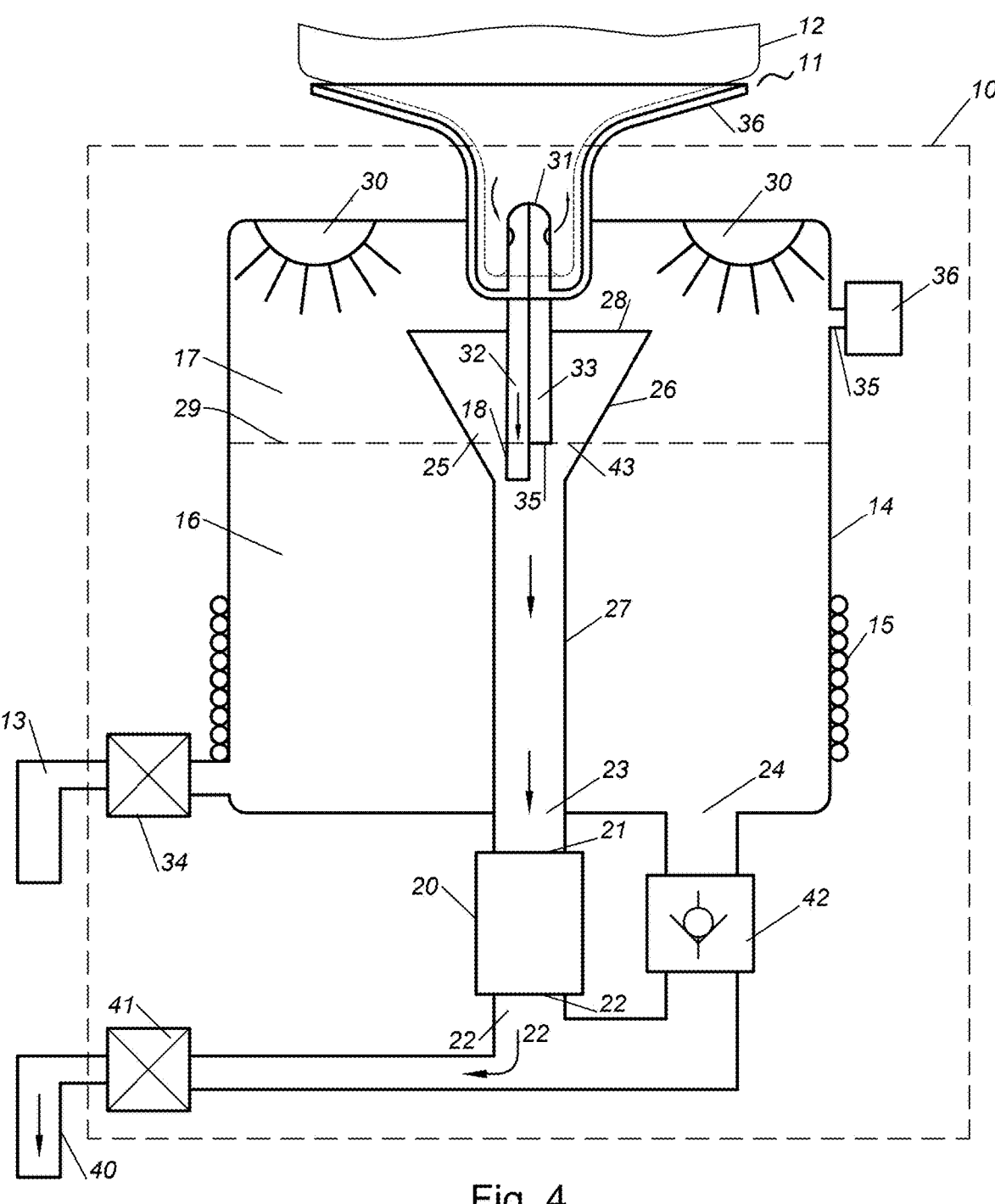
FIG. 4 schematically shows the interior design of another embodiment the dispenser.

FIG. 4 shows another embodiment of the dispenser. The dispenser in FIG. 4 differs from the dispenser in FIG. 3 in that it additionally contains the tap 40 for dispensing uncooled sterilized water to consumers. The tap 40 for dispensing uncooled water through the solenoid valve 41 is connected to the outlet 22 of the flow sterilizer 20. The check valve 42 is installed before the inlet 24 for sterilized water in the tank 14, which passes the water coming from the flow sterilizer 20 into the cold water tank 14, but prevents the outflow of sterilized water from the tank 14 into the path for uncooled water in uncooled sterilized water dispensing mode through the tap 40.

When the dispenser is operating, the valve 41 opens to dispense uncooled water to consumers and the water from the funnel 25 comes to the tap 40 through the outlet 23 and the flow sterilizer 20. When water flows out of the funnel 25, the water level 43 in the funnel 25 falls, thereby opening the inlet 35 of the air channel 32 of the water intake finger 31 and the water flowing out of the bottle 12 through the funnel 25 and the flow sterilizer comes to the tap 40. After closing of the valve 41, the water level in the funnel 25 is restored to the original value corresponding to the water level 29 in the cold water tank 14.

In this way, the uncooled water dispensed to consumers is also sterilized. Besides, the dispensing of uncooled water to consumers does not affect the operation of the cold water tank. This design is also convenient in that adding the possibility of dispensing uncooled water to consumers does not require redesigning of the dispenser.

When dispensing cooled water to consumers, this dispenser operates similarly to the previously described dispenser in FIG. 3.

Figure 5:
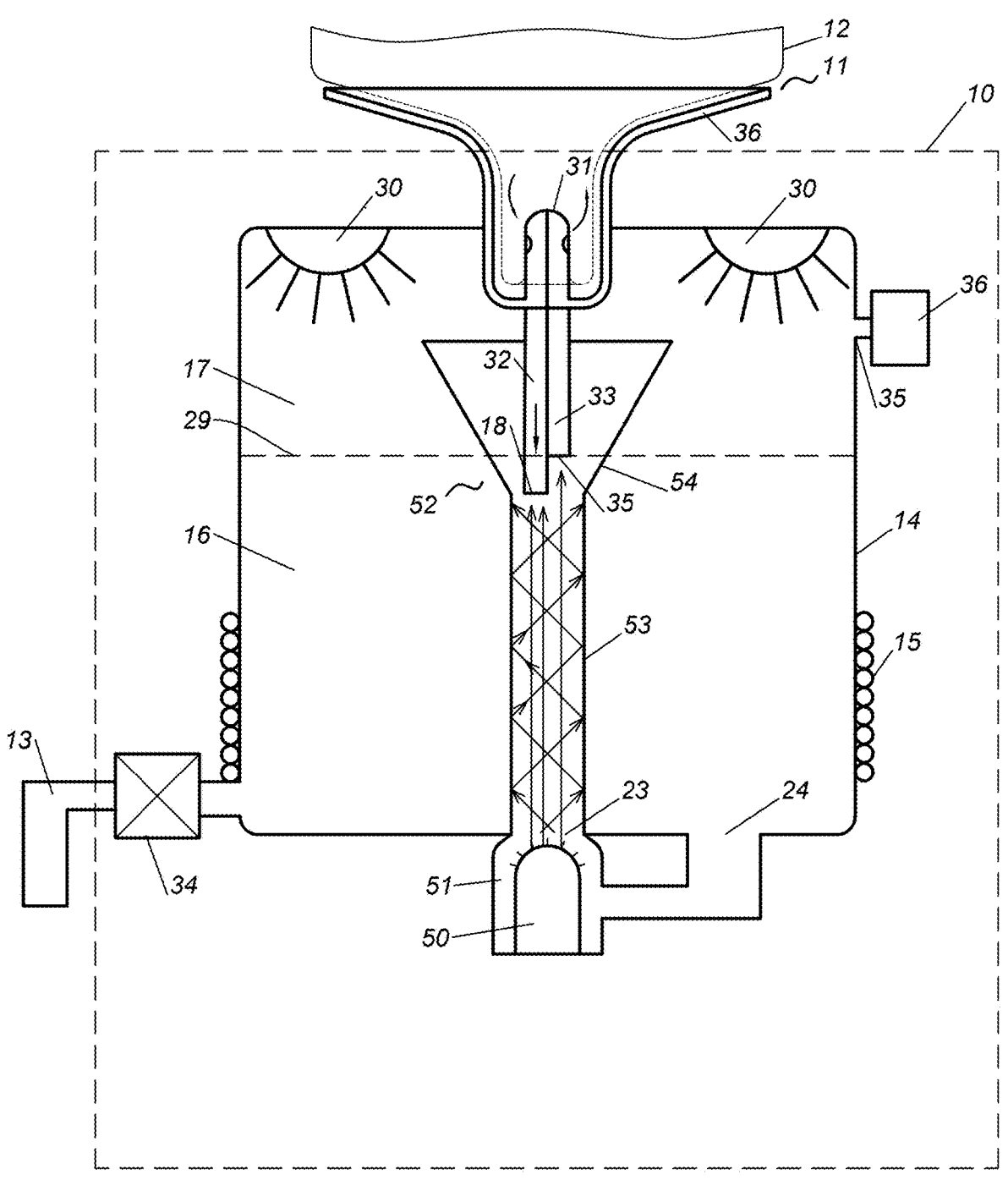
FIG. 5 schematically shows the interior design of yet another embodiment of the dispenser.

FIG. 5 shows yet another embodiment of the dispenser. The dispenser in FIG. 5 differs from the dispenser in FIG. 3 with the design of flow sterilizer. In this implementation, the flow sterilizer contains the UV radiation source 50, which is located inside the chamber 51 connected to the outlet 23 of the cold water tank 14. The UV radiation source 50 is located in such a way that its radiation comes to the lower part 53 of the funnel 52. The lower part 53 of the funnel 52 is made in the form of a vertical pipe. The water flowing through the funnel 52 is sterilized by ultraviolet radiation from the source 50 during the flowing through the lower part 52 and through the chamber 51. It is preferable to use a narrowly directed UV radiation source 50 so that part of its radiation also comes from below of the water intake finger 31 to sterilize it.

Otherwise, this dispenser does not differ from the dispenser described previously and shown in FIG. 3.

Figure 2:
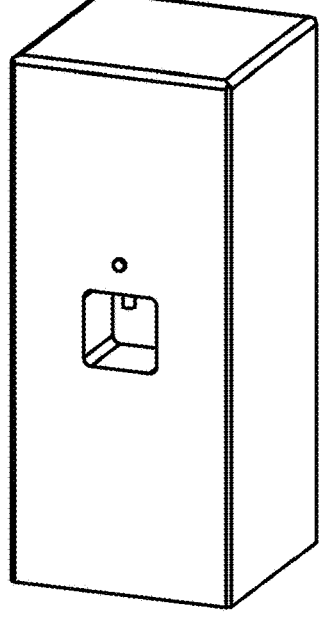
FIG. 2 shows a general view of the dispenser connected to the water-pipe.
Figure 6:
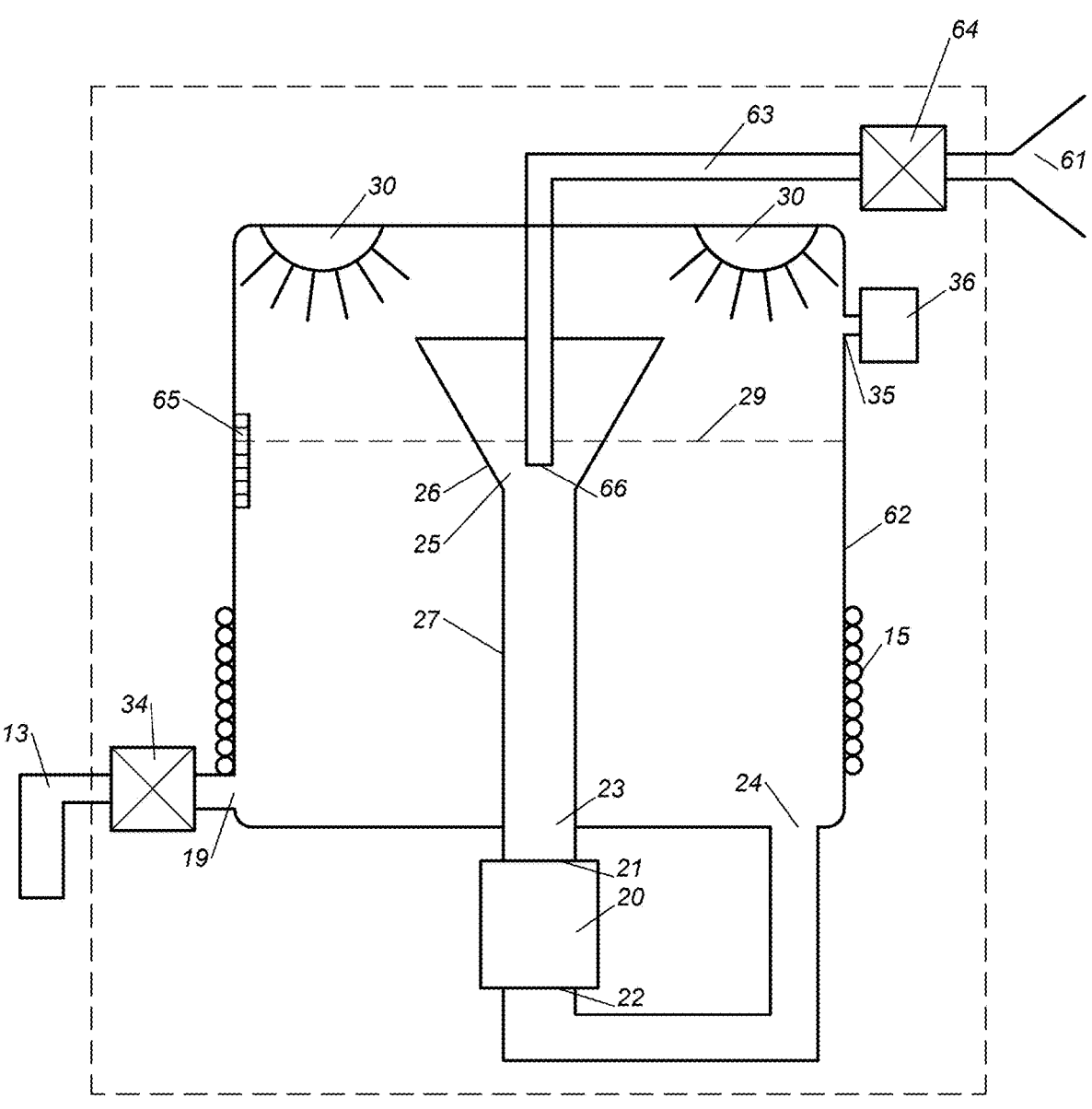
FIG. 6 schematically the interior design of the dispenser connected to the water-pipe.

FIG. 6 shows still another embodiment of the dispenser. A general view of this dispenser is shown in FIG. 2. This is a dispenser connected to an external water source. Such external source can be, for example, a bag-in-box water package located on top of the device or a free-standing water container or municipal water-pipe.

This dispenser differs from the dispenser described previously and shown in FIG. 3 in that water from the external source 61 enters the cold water tank 62 through the pipeline 63, under the lower end of which 66 is located the funnel 25. Water level in the tank 62 is controlled by the electronic control device (not shown) opening and closing the solenoid valve 64 installed in the pipeline 63 depending on the signal coming from the water level sensor 65 installed in the cold water tank 62.

Otherwise, this dispenser does not differ from the dispenser described previously and shown in FIG. 3.

This design is also convenient in that the dispenser with the external source does not differ much from the dispenser using the upturned bottle as the source, which allows using common parts for both types of water dispensers and does not complicate the design of the dispenser much.

REFERENCE SIGNS LIST

10 housing
11 device for connection to the water source
12 water source (bottle)
13 tap for dispensing cooled water
14 cold water tank
15 cooling device
16 lower part of the cold water tank
17 upper part of the cold water tank

18 inlet for water coming from the source
19 cooled water outlet
20 flow sterilizer
21 inlet of the flow sterilizer
22 outlet of the flow sterilizer
23 uncooled water outlet
24 sterilized water inlet
25 funnel
26 wide upper part of the funnel
27 narrow lower part of the funnel
28 upper edge of the funnel
29 water level in the cold water tank
30 UV radiation source (in the cold water tank)
31 water intake finger
32 water channel
33 air channel
34 solenoid valve
35 inlet of the air channel of the water intake finger
36 bottle receiver
40 tap for dispensing uncooled water to consumers
41 solenoid valve (tap for dispensing uncooled water)
42 check valve
43 water level in the funnel
50 UV radiation source located inside
51 chamber
52 funnel
53 lower part of the funnel
54 upper part of the funnel
61 external source
62 cold water tank (POU)
63 pipeline
64 solenoid valve
65 water level sensor
66 lower end of the pipeline

The invention claimed is:

1. A drinking water dispenser with built-in UV sterilization system, comprising:

a housing (10);

a device (11) for connecting to a water source (12);

a tap (13) for dispensing cooled water to consumers;

a cold water tank (14) arranged in the housing (10), wherein the cold water tank (14) is equipped with a cooling device (15), wherein the cold water tank (14) has a lower part (16) to be filled with the cooled water and an upper part (17) where an air cavity is formed when the cold water tank (14) is filled with the cooled water, wherein the cold water tank (14) has an inlet (18) for uncooled water coming from the water source (12) connected to the device (11) for connecting to the water source (12), wherein at least one UV radiation source (30) is installed inside the cold water tank (14), wherein the cold water tank (14) has a cooled water outlet (19) connected to the tap (13), and wherein the cold water tank (14) is equipped with an outlet for the uncooled water (23) and a sterilized water inlet (24);

a flow sterilizer (20) having an inlet (21) and an outlet (22), wherein the inlet (21) of the flow sterilizer (20) is connected to the outlet for the uncooled water (23), and the outlet (22) of the flow sterilizer (20) is connected to the sterilized water inlet (24); and a funnel (25) having a wide upper part (26) and a narrow lower part (27) installed inside the cold water tank (14), wherein the funnel (25) is installed under the inlet (18) for the uncooled water coming from the water source (12), so that an upper edge (28) of the funnel (25) is above a water level (29) in the cold water tank (14), to isolate the cooled water in the lower part (16) of the cold water tank (14) from the uncooled water coming from the water source (12), and wherein the narrow lower part (27) of the funnel (25) is connected to the outlet for the uncooled water (23).

2. The drinking water dispenser according to claim 1, wherein the device (11) for connecting to the water source (12) comprises:

a bottle receiver (36) for installation of an upturned bottle, and a water intake finger (31) with a water channel (32) which forms the inlet (18) for the uncooled water coming from the water source (12).

3. The drinking water dispenser according to claim 1, wherein the device (11) for connecting to the water source (12, 61) comprises means for connecting to a bag-in-box water source.

4. The drinking water dispenser according to claim 1, wherein the device (11) for connecting to the water source (12, 61) comprises means for connecting to a water-pipe.

5. The drinking water dispenser according to claim 1, comprising a water level sensor (65) in the cold water tank (14) connected to an electronic control device.

6. The drinking water dispenser according to claim 1, further comprising:

a further tap (40) for dispensing the uncooled water to consumers, the further tap (40) being connected to the outlet (21) of the flow sterilizer (20); and a check valve (42) installed between the flow sterilizer (20) and the sterilized water inlet (24).

7. The drinking water dispenser according to claim 1, wherein said at least one UV radiation source (30) installed in the cold water tank (14) is installed in the upper part (17) of the cold water tank (14).

8. The drinking water dispenser according to claim 7, wherein said at least one UV radiation source (30) in the cold water tank (14) is located in such a way that part of its radiation reaches the funnel (25).

9. The drinking water dispenser according to claim 1, wherein the flow sterilizer (20) is positioned in such a way that part of UV radiation from the flow sterilizer (20) reaches the lower part (27) of the funnel (25).

10. The drinking water dispenser according to claim 9, wherein the lower part (27) of the funnel (25) is a vertical pipe.

11. The drinking water dispenser according to claim 9, wherein inner walls of the lower part (27) of the funnel (25) are made of a material reflecting UV radiation.

12. The drinking water dispenser according to claim 1, wherein the flow sterilizer (20) is at least partially located in the cold water tank (14).

\* \* \* \* \*